United States Patent [19]

Sarno et al.

[11] Patent Number: 5,945,098
[45] Date of Patent: *Aug. 31, 1999

[54] STABLE INTRAVENOUSLY-ADMINISTRABLE IMMUNE GLOBULIN PREPARATION

[75] Inventors: Maria Erlinda C. Sarno, Cerritos; Rodolfo Anthony Vasquez, Norwalk; Sau-Gee Yung, Rialto; Clifford R. Graf, Lakeview Terrace, all of Calif.

[73] Assignee: Baxter International Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/935,294

[22] Filed: Sep. 22, 1997

Related U.S. Application Data

[63] Continuation of application No. 08/504,854, Jul. 20, 1995, abandoned, which is a continuation of application No. 08/317,214, Oct. 3, 1994, abandoned, which is a continuation of application No. 08/178,432, Jan. 6, 1994, abandoned, which is a continuation of application No. 07/866,089, Apr. 6, 1992, abandoned, which is a continuation of application No. 07/473,554, Feb. 1, 1990, abandoned.

[51] Int. Cl.⁶ .................................................. A61K 38/21
[52] U.S. Cl. ............................... 424/85.5; 514/2; 514/12; 514/21; 530/387.1; 530/389.1; 530/380; 530/390.5
[58] Field of Search ............................... 424/85.5; 514/2, 514/12, 21; 530/387.1, 389.1, 380, 390.5

[56] References Cited

U.S. PATENT DOCUMENTS

| | | | |
|---|---|---|---|
| 3,903,262 | 9/1975 | Pappenhagen et al. | 424/85 |
| 4,165,370 | 8/1979 | Coval | 424/85.8 |
| 4,168,303 | 9/1979 | Nishida et al. | 530/387 |
| 4,186,192 | 1/1980 | Lundblad et al. | 424/85.8 |
| 4,362,661 | 12/1982 | Ono et al. | 424/85.1 |
| 4,371,520 | 2/1983 | Uemura et al. | 424/85.8 |
| 4,374,763 | 2/1983 | Takagi | 424/85.8 |
| 4,384,993 | 5/1983 | Sato et al. | 424/85.1 |
| 4,396,608 | 8/1983 | Tenold | 424/85.8 |
| 4,439,421 | 3/1984 | Hooper et al. | 424/85 |
| 4,477,432 | 10/1984 | Hardie | 424/85.1 |
| 4,482,483 | 11/1984 | Curry et al. | 530/387 |
| 4,540,573 | 9/1985 | Neurath et al. | 424/85 |
| 4,565,651 | 1/1986 | Ohmura et al. | 514/8 |
| 4,597,966 | 7/1986 | Zolton et al. | 424/85.8 |
| 4,613,501 | 9/1986 | Horowitz | 424/89 |
| 4,623,717 | 11/1986 | Fernandes et al. | 530/381 |
| 4,637,834 | 1/1987 | Thurow | 514/3 |
| 4,639,513 | 1/1987 | Hou et al. | 530/387 |
| 4,692,331 | 9/1987 | Uemura et al. | 424/85 |
| 4,719,290 | 1/1988 | Curry et al. | 530/357 |
| 4,721,777 | 1/1988 | Uemura et al. | 530/388.15 |
| 4,764,369 | 8/1988 | Neurath et al. | 424/89 |
| 4,789,545 | 12/1988 | Woods et al. | 424/101 |
| 4,876,088 | 10/1989 | Hirao et al. | 424/85.8 |
| 4,877,608 | 10/1989 | Lee et al. | 424/85.8 |
| 5,177,194 | 1/1993 | Saras et al. | 530/412 |

FOREIGN PATENT DOCUMENTS

| | | |
|---|---|---|
| 0187712 | 7/1986 | European Pat. Off. . |
| 0196761 | 10/1986 | European Pat. Off. . |
| 2500076 | 7/1976 | Germany . |
| 53-47515 | 4/1978 | Japan . |
| 55-164630 | 12/1980 | Japan . |
| 59-97057 | 6/1984 | Japan . |

OTHER PUBLICATIONS

Tomono et al., Vox Sang vol. 51 (2) pp. 81–86 (1986).
Stephan, W., "Undegraded Gamma–Globulin for Intravenous Therapy: A New Preparation of Immune Serum Globulin for Intravenous Administration," *XXIVth Scientific Meeting of the Blood Research Institute*, pp. 469–478, 1971.
Fernandes et al., "Preparation of a Stable Intravenous Gamma–Globulin: Process Design and Scale–Up," *Vox Sang.* 39: 101–12 (1980).
Gerber, "Stabilization of Gamma Globulin with Copper Complexes: Possible Relevance to the Etiology of Rheumatoid Arthritis," *Inflammation Diseases and Copper* (1982).
Gerber, "Inhibition of Denaturation of Human Gamma Globulin by a Mixture of L–Histidine, L–Cystine, and Copper, and Its Clinical Implication in Rheumatoid Arthritis," *Arthritis and Rheumatism*, vol. 19, 3:593–601 (1976).
Florence et al., "Emulsion Stabilization by Non–Ionic Surfactants: Experiment and Theory," *J. Pharm. Pharmac.* 23:153–169 (1971).
Miller, G., et al., "Stabilization of Cytotoxic Antibody and Complement with Cysteine," *J. of Immun.*, vol. 101, No. 5, pp. 1074–1077 (1968).

*Primary Examiner*—Chhaya D. Sayala
*Attorney, Agent, or Firm*—Rothwell, Figg, Ernst & Kurz, p.c.

[57] ABSTRACT

Stable, intravenously-administrable immune globulin preparations are stabilized against aggregation and polymerization and rendered isotonic with amino acid(s) and non-ionic detergents, polysorbate and polyethylene glycol. The immunoglobulins are derived from human or animal sources, or from hybridomas. Optional, additional stabilizers include various physiologically-acceptable carbohydrates and salts. Polyvinylpyrrolidone can be used in addition to the amino acid(s). Apart from the immunoglobulin itself, the preparations are otherwise essentially protein free. The preparations are useful in immunotherapy and as diagnostic reagents.

15 Claims, No Drawings

STABLE INTRAVENOUSLY-ADMINISTRABLE IMMUNE GLOBULIN PREPARATION

This is a continuation of Ser. No. 08/504,854 filed on Jul. 20, 1995 now abandoned, which is a continuation of Ser. No. 08/317,214 filed Oct. 3, 1994, now abandoned, which is a continuation of Ser. No. 08/178,432, filed Jan. 6, 1994, now abandoned, which is a continuation of Ser. No. 07/866,089, filed Apr. 6, 1992, now abandoned, which is a continuation of Ser. No. 07/473,554, filed Feb. 1, 1990, now abandoned.

BACKGROUND OF THE INVENTION

1. Technical Field

The present invention relates to intravenously-administrable immune globulin preparations. More specifically, the invention relates to immune serum globulin preparations that, aside from the immune globulin itself, are otherwise essentially protein free. The preparations are administrable by other routes as well. The preparations also are useful reagents for diagnostic testing and can be supplied in their solution form in diagnostic test kits.

The term immune globulin, also known as Immunoglobulin G, IgG and gamma globulin, encompasses both immune serum globulin and monoclonal immune globulins. Immune serum globulin is obtained from pooled plasma samples from either normal or hyperimmune donors and contains IgG antibodies to many common bacterial and viral infectious agents. Monoclonal immune globulins (monoclonal antibodies) are obtained from hybridomas.

Immune globulin long has been used in connection with the prophylaxis and treatment of a variety of diseases and disorders. Certain patients with immunodeficiencies are rendered susceptible to acute and chronic infections, with life-threatening consequences, which the immune system of the normal patient can easily combat. These patients with compromised immune systems are not able to produce normal levels of antibodies and can greatly benefit from the administration of exogenous immune globulin.

Patients with normal immune systems and antibody levels may require additional defense in overcoming certain antibiotic-resistant bacterial infections, such as those caused by *Pseudomonas aeruainosa*. Immunotherapy via the administration of immune globulin has become a standard treatment in these circumstances.

The administration of immune globulin is perhaps most widespread in the prophylaxis of what were once highly common diseases. Many viral infections, such as German measles, measles, mumps and smallpox, for example, can be controlled via the widespread administration of the appropriate immune globulins to children. The occurrence of many bacterial infections also have been controlled or virtually eliminated due to the widespread administration of immune globulins.

Immune serum globulins for human administration were first produced via an alcohol fractionation method developed by E. Cohn et al., J. Amer. Chem. Soc. 68: 459 (1946). These preparations contained approximately ten to eighteen (wt.) percent protein and were relatively stable during storage at 2 to 8° C. Although originally intended for intravenous administration, it was found that untoward reactions, including anaphylactic shock, rendered unsafe such administration of the alcohol fractionated immune serum globulins. These products are acceptable for intra-muscular injection, however.

A particularly preferred method for producing an immune globulin fraction from Cohn Fractions I+II+III, for use in the present invention, is disclosed in U.S. Pat. No. 5,177,194 filed concurrently herewith and incorporated by reference herein.

Although intramuscular injection of immune globulin can effectively raise circulating antibody levels in most patients, this mode of administration suffers from several disadvantages. The antibodies administered in this manner diffuse rather slowly into the circulation. The ultimate blood levels attained from a given dose varies from patient to patient, and local tissue injury at the injection site is a possibility. Moreover, only a fraction of the total immune globulin administered to the patient reaches the bloodstream.

The intravenous administration of immune globulin overcomes these disadvantages. The desired level of circulating antibody is reached almost instantaneously and can be relatively accurately controlled by control of the dosage. Effectively larger doses can be more quickly administered without the discomfort associated with intramuscular injection.

As mentioned earlier, the intravenous injection of certain immune globulin preparations has lead to severe reactions. These reactions are generally believed to be caused by the activation of complement by aggregates and/or fragments of immunoglobulin which form during the preparation and/or storage of the immune globulin product. Thus, the safe administration of immune globulin requires steps to be taken to avoid the formation of immunoglobulin fragments and agglomerates and their resulting anticomplement activity.

Immune globulins (antibodies) also find wide use in the diagnostics field. Diagnostic test kits, intended for a single use, often contain a monoclonal antibody preparation as one of the test reagents. These antibody preparations are commonly provided in lyophilized form in order to increase their shelf life, and must be reconstituted just prior to use. The immune globulin preparations of the present invention, however, are quite stable and are well suited to being included in diagnostic test kits in their solution form.

2. Description of the Prior Art

The processing of immune globulin preparations in order to reduce anticomplement activity is documented in the literature. In "Preparation of a Stable Intravenous Gamma-Globulin: Process Design and Scale Up", Fernandes, P. M. and Lundblad, J. L., Vox Sang. 39: 101–112 (1980), the authors note that a variety of such processing methods have been investigated. The various techniques are (a) removal of high-molecular-weight aggregates by centrifugation, (b) pH adjustment to 4.0, (c) 'gentle' fractionation techniques, (d) affinity methods, (e) use of protein stabilizers and (f) enzymatic treatment and other chemical modifications. None of these methods has been entirely successful from either the purely medical or commercial viewpoints, however. For example, the various chemical treatments can alter the immunoglobulin's physical structure and hence its activity. Some treatments for disassociating immunoglobulin agglomerates are not permanent; the agglomerates reappear during storage or during pH shifts to physiological conditions.

Japanese Kokai No. 60-146832 (1985) discloses that IgG preparations prepared via the cold ethanol fractionation and ammonium sulfate fractionation methods contain from 10 to 40 percent aggregated IgG in addition to 7S IgG. These preparations are unsuitable for intravenous administration because of their anticomplement activating effects. It is reported that these same preparations, after treatment by maintenance at pH 3.7 to 4.3 at 1 to 10° C. over the course of 0.5 to 20 hours, no longer exhibit anticomplement activity. A stabilizing compound selected from among various inorganic salts, sugars, proteins and organic acid salts is added to prevent denaturation of the immunoglobulin chain during the acid treatment.

U.S. Pat. No. 4,719,290 (Curry et al.; Jan. 12, 1988) provides a reportedly intravenously-administrable gamma globulin preparation by stabilizing a purified Cohn Fraction II with relatively large amounts of human serum albumin. The final solution is formulated with the addition of sodium chloride and/or a carbohydrate.

U.S. Pat. No. 4,396,608 (Tenold et al.; Aug. 2, 1983) relates to a process for stabilizing immune serum globulin preparations so as to avoid aggregation. The pH of a Fraction II (or other Cohn fraction) filtrate is adjusted to 3.5–5.0 and the ionic strength is then adjusted (lowered) via filtration, dialysis, etc. or combinations thereof. The solution is then made isotonic via the addition of an amino acid, a carbohydrate or a sugar.

U.S. Pat. No. 4,093,606 (Coval; Jun. 6, 1978) relates to fractionation techniques whereby a suspension of Cohn Fraction II or II+III plasma protein is reportedly rendered stable for intravenous injection. Preparations are formulated with glycine, albumin and a non-ionic surfactant such as one of the polysorbates.

Although albumin is known for its ability to stabilize proteins in solution, its stabilizing properties diminish with time. Other factors also detract from the use of albumin. The presence of serum-derived albumin in a preparation may detract from its overall purity, as it is now well known that many contaminants, including proteins and infectious agents, can be neither easily detected nor removed with certainty in a cost effective manner. The presence of albumin also can mask the presence of immunoglobulin fragments in the immune serum. If such fragments are present, yet undetected, the presence of undesirable enzymes which produce such fragments also may go undetected. Thus, a need exists for improved stabilized immune globulin preparations which are albumin-free.

SUMMARY OF THE INVENTION

In one of its aspects the present invention relates to a stable, intravenously-administrable immune globulin preparation comprising an aqueous solution of immune globulin, an amount of an amino acid effective to impart a physiologically-acceptable tonicity to the preparation and to maintain the immune globulin in monomeric form, and a physiologically-acceptable amount of a non-ionic detergent wherein, apart from the immune globulin itself, the preparation is essentially protein-free.

In another aspect, the present invention relates to a stable, intravenously-administrable immune globulin preparation comprising an aqueous solution of immune globulin, a physiologically acceptable amount of polyvinylpyrrolidone effective to maintain said immune globulin in monomeric form, an amount of a carbohydrate or a physiologically acceptable salt or an amino acid effective to impart a physiologically-acceptable tonicity to the preparation, and a physiologically-acceptable amount of a non-ionic detergent wherein again the preparation is essentially protein-free apart from the immune serum globulin.

The present invention advantageously provides a storage-stable liquid product, thus eliminating the inconvenience and expense of lyophilization and reconstitution. The ionic strength, pH and protein concentration can be optimized during processing, and the final product can be stored at ambient temperatures or under refrigeration. The stabilizers are non-toxic and present in minimal amounts, and they do not alter the native biological form or function of the immunoglobulin. Polymerized immunoglobulin does not form during storage; thus, the preparations are well suited for intravenous administration. The preparations also are useful as stable immune globulin reagents for use in diagnostic applications.

DETAILED DESCRIPTION OF THE INVENTION

The immune globulin preparations according to the present invention are prepared from any starting materials based on native or monoclonal immunoglobulin G. The teachings herein are applicable to immunoglobulins derived from both native and monoclonal sources. Most frequently the preparations will be prepared from gamma globulin-containing products produced by the alcohol fractionation and/or ion exchange and affinity chromatography methods well known to those skilled in the art. Purified Cohn Fraction II is commonly used and is the starting point for the preparations disclosed herein unless otherwise noted.

As accepted in the art, the starting Cohn Fraction II paste is about 95 percent pure IgG and is comprised of each of the four subclasses of IgG, namely, $IgG_1$, $IgG_2$, $IgG_3$ and $IgG_4$. The different subclasses are present in Fraction II in approximately the same ratio as they are found in the pooled human plasma from which they are obtained. The Fraction II must be further purified before formulation into an administrable product, and this can be accomplished via any of a number of known procedures so that the final immune serum globulin product does not contain impurities, such as IgG polymers and/or fragments, that possess anticomplement activities.

For example, the Fraction II paste can be dissolved in a cold purified aqueous alcohol solution and impurities removed via precipitation and filtration. Following the final filtration the immunoglobulin suspension is diafiltered using ultrafiltration membranes having a nominal molecular weight limit of $\leq 100,000$ daltons to remove the alcohol. The solution is either concentrated or diluted to obtain the desired protein concentration and can be further purified by techniques well known to those skilled in the art.

A physiologically acceptable amount of a non-ionic detergent is added to the immunoglobulin solution in accordance with the present invention. By 'physiologically acceptable' it is meant that the amount added is a stabilizing, non-toxic amount low enough to avoid any adverse toxic reactions as derived from known LD50 values and/or published literature pertinent to the potential toxicity of the particular additive. It is advantageous to use the least amount necessary to produce the desired stabilization. The detergent reduces the tendency of the immunoglobulin molecules to come out of solution. Suitable detergents (surfactants) include the partial esters of sorbitol and polyoxyethylene oxides of long chain fatty acids known as the polysorbates, alkylpolyethoxyethanols and alkarylpolyethoxyethanols. Polysorbate 80, commercially available as Tween™ 80 from Atlas Chemical Industries, is most preferred. The non-ionic detergents are advantageously used in minimal amounts and preferably below about 0.01 percent (w/v). It has been found that from 0.0005 to 0.01 percent is useful, and final products containing about 0.002 percent (w/v) of non-ionic detergent are preferred when the immune serum globulin content is 5 percent (w/v). At higher immune serum globulin concentrations, for example 10 percent, the detergent level (i.e. detergent concentration to protein ratio) can be reduced even further. At these higher protein concentrations the immunoglobulin molecules appear to stabilize themselves. The optimal detergent content is obtained by formulation experiments well known to those skilled in the art. In any case, it appears that a desirable detergent concentration provides a balance of hydrophilic and hydrophobic properties to the protein solution so that the immunoglobulin is less prone to denature. The optimal detergent concentration will be the minimal amount that will prevent particles from coming out of solution, will not cause toxic effect and will not adversely alter the efficacy of the final product under the selected storage conditions.

An amount of one or more amino acids effective to impart a physiologically-acceptable tonicity (i.e. about 300 mOsm/l) to the preparation and to maintain said immune serum globulin in monomeric form also is added to the solution. Preferred amino acids include glycine, lysine, arginine and phenylalanine, with glycine being particularly preferred. A glycine concentration of about 0.2 M generally is preferred.

The IgG solution can further comprise polyvinylpyrrolidone ("PVP") at certain pH ranges, typically pH 4 to pH 7, in addition to or in place of the amino acid(s) as an agent for preventing polymerization and/or particulation of the gamma globulin. PVP alone typically does not provide long term stabilization of immunoglobulins, but PVP does contribute to effective long term stabilization in the preparations of this invention. The amount of PVP useful in the preparations is limited by its toxicity and insolubility at high concentrations. From 0.1 to 1 percent (w/v) of PVP K-15 (or other water soluble grade) is useful to prevent particulation. Amounts within this range are soluble and well below toxic levels.

The addition of PVP does not provide an isotonic solution (except when the PVP is added at unacceptably high levels). Therefore, PVP generally is added to the IgG solutions in combination with other additives such as amino acids, physiologically-acceptable salts or carbohydrates which can be used to adjust for isotonicity. Useful carbohydrates include sugars such as dextrose, mannose, trehalose, galactose, dextran, fructose, lactose, sucrose, maltose, mannitol and sorbitol. Non-reducing carbohydrates are preferred. Almost any physiologically acceptable salt, such as sodium chloride, sodium acetate, sodium citrate, etc., can be used to adjust the tonicity of the preparations. Examples include the alkali metal, alkaline earth metal, ammonium and phosphate salts as well as various organic salts (including but not limited to oxalate, valerate, oleate, laurate, borate, benzoate, lactate, tosylate, citrate, maleate, fumarate, succinate and tartrate). Sodium chloride and sodium citrate are preferred salts. The specific amount of any particular tonicity-adjusting agent(s) needed to provide an isotonic solution will vary from preparation to preparation. The artisan will readily determine appropriate amounts, however.

It has been found that the pH of the immune globulin preparation is an important factor relative to the IgG monomer content of the final product. In the preparations of the present invention the pH can range from 4.0 to 7.4. Within this range, a lower pH is desired, however, to ensure maximum monomer content. A pH of 4.2±0.5 is preferred for a 5 percent immune serum globulin preparation. Ten percent preparations, however, are most stable at a pH of 5.2±0.2. Optimal pH is obtained by formulation techniques well known to those skilled in the art. For example, optimal pH can be determined from size exclusion chromatography determinations as well as heat stability data and anticomplement titers of the various preparations under differing pH conditions.

Immune globulin solutions, including immune globulin solutions useful as starting materials for the present preparations, often include minor amounts of poly(ethylene glycol) ("PEG") as a stabilizer. While PEG alone cannot provide a preparation as stable as those described herein, its presence is believed to be important to the overall stability of any immune globulin solution, including those of the present invention. Thus, if PEG is not already present in the starting source of immune globulin, a small amount (typically less than 0.2 gram %) should be included in the preparations of the invention.

It will be apparent that the appropriate concentrations of the various stabilizers in the present immune globulin compositions will vary with protein concentration. Normal variations among pooled sera also will cause adjustments in stabilizer requirements. Those skilled in the art will readily determine acceptable stabilizer levels based on the teachings herein.

The invention is illustrated by the following Examples. All percentages are by weight unless otherwise noted.

EXAMPLE I

Glycine at concentrations of 0.2±0.1M is added to aqueous IgG solutions purified according to the method taught in U.S. Pat. No. 5,177,194 from Cohn Fr. I+II+III, or other more crude IgG sources which contain residual amounts of polyethylene glycol, usually less than 0.2 g %. The protein concentration is then adjusted to approximately 5% either by dissolution and dilution of a purified IgG precipitate or concentration through the use of tangential flow ultrafiltration and other suitable means of concentrating proteins. The pH is adjusted to 5.0±1.0 and Polysorbate 80 (Tween™ 80) is then added to a 0.003±0.001% level. The IgG solution is sterile filtered and filled into final containers for use.

EXAMPLE II

Glycine at concentrations of 0.2±0.1M is added to aqueous IgG solutions purified from Cohn Fr. II, Cohn Fr. III filtrate, or other more crude IgG sources. The protein concentration is then adjusted to approximately 10% and the pH is adjusted to 6.0±1.0. Polysorbate 80 (Tween™ 80) is then added to a 0.007±0.003% level. The IgG solution is sterile filtered and filled into final containers for use.

EXAMPLE III

Glycine at concentrations of 0.2±0.1M, PEG at concentrations of 0.01% and polysorbate at concentrations of approximately 0.001% are added to an aqueous solution of purified monoclonal antibody derived from hybridomas. The concentration of the antibody is approximately 2 mg/ml and the solution is kept at pH 5.2 using 10 mM sodium citrate or sodium phosphate as buffer. This preparation can be used as a diagnostic reagent or can be sterile filtered and filled into final containers for intravenous or intramuscular administration.

EXAMPLE IV

Glycine at concentrations of 0.2±0.1M, and polyvinylpyrrolidone at concentrations ranging from 0.1 to 1% is added to aqueous IgG solutions purified from Cohn Fr. II, Cohn Fr. III filtrate, or other more crude IgG sources which contain residual amount of PEG (typically less than 0.2%). The protein concentration is then adjusted to the desired value, usually 5 or 10%, by known dilution or concentration techniques such as ultrafiltration. The pH is adjusted to 5.0±1.0. Polysorbate 80 (Tween™ 80) is then added to a concentration that will not cause particulation in the solution, typically, 0.003±0.001 for 5% protein solution or 0.007%±0.003% for a 10% protein solution. The IgG solution is sterile filtered and filled into final containers for use.

EXAMPLE V

Glycine at concentrations of 0.2±0.1M and carbohydrates such as trehalose, glucose, mannitol, hydroxyethyl starch, carboxy methyl cellulose, hydroxymethyl starch, maltose, glycerol, lactose etc. at concentrations of 0.1 to 3% is added to aqueous IgG solutions purified from Cohn Fr. II, Cohn Fr. III filtrate, or other more crude IgG sources which contain residual amount of PEG, typically less than 0.2 g %. The protein concentration is then adjusted to the desired concentration, usually 5 or 10%, by known dilution or concentration techniques such as ultrafiltration. The pH is adjusted to 5.0±1.0. Polysorbate 80 (Tween™ 80) is then added to a concentration that will not cause particulation in the solution, typically 0.003±0.001% for a 5% protein solution or 0.007±0.003% for a 10% protein solution. The IgG solution is sterile filtered and filled into final containers for use.

Although the invention has been described in connection with certain preferred embodiments, it is not so limited. Variations within the scope of the claims will be apparent to those skilled in the art.

We claim:

1. A storage stable, intravenously-administrable immune globulin preparation comprising an aqueous solution of immune globulin, from about 0.1 M to about 0.3 M glycine, from about 0.0005% (w/v) to about 0.01% (w/v) polysorbate, and less than about 0.2 gram % PEG, wherein the preparation is essentially protein-free apart from said immune globulin.

2. An immune globulin preparation according to claim 1 wherein said polysorbate detergent is polysorbate 80.

3. An immune globulin preparation according to claim 2 wherein the immune globulin concentration is about 5 percent (w/v) and the concentration of polysorbate 80 is about 0.002 percent (w/v).

4. An immune globulin preparation according to claim 1 wherein the immune globulin concentration is about 5 percent (w/v) and the concentration of polysorbate is about 0.002 percent (w/v).

5. An immune globulin preparation according to claim 1 having a glycine concentration of about 0.2 M.

6. An immune globulin preparation according to claim 1 having an immune globulin concentration of about 5% (w/v) and a pH of about 4 to 7.4.

7. An immune globulin preparation according to claim 1 having an immune globulin concentration of about 10% (w/v) and a pH of about 5 to 7.4.

8. An immune globulin preparation according to claim 1 further comprising a carbohydrate or a physiologically acceptable salt.

9. An immune globulin preparation according to claim 8 wherein said carbohydrate is selected from the group consisting of dextrose, mannose, trehalose, galactose, dextran, fructose, sucrose, maltose, mannitol and sorbitol.

10. An immune globulin preparation according to claim 1 wherein the immune globulin is derived from a monoclonal source.

11. An immune globulin preparation according to claim 1 wherein the immune globulin concentration is about 10 percent (w/v) and the polysorbate detergent concentration is from about 0.0005 to less than about 0.002 percent (w/v).

12. A storage stable, intravenously-administrable immune globulin preparation according to claim 1 wherein the polysorbate is present from about 0.002% (w/v) to about 0.01% (w/v).

13. A method for preparing a storage stable intravenously-administrable immune globulin preparation comprising imparting a physiological tonicity to an aqueous immunoglobulin solution by adding from about 0.1 M to about 0.3 M glycine, from about 0.0005% (w/v) to about 0.01% (w/v) polysorbate, and less than about 0.2 gram % PEG, thereto, said preparation being essentially protein-free apart from said immune globulin.

14. A method according to claim 13 wherein the polysorbate is added in an amount from about 0.002% (w/v) to about 0.01% (w/v).

15. A method according to claim 13 further comprising the addition of a physiologically acceptable amount of polyvinylpyrrolidone effective to maintain said immune globulin in monomeric form.

* * * * *